(12) United States Patent  
Lietz et al.

(10) Patent No.: US 11,986,214 B2
(45) Date of Patent: May 21, 2024

(54) TROCAR WITH DETACHABLE LIGHTING SYSTEM

(71) Applicant: KARL STORZ SE & Co. KG, Tuttlingen (DE)

(72) Inventors: Daniel Lietz, Santa Barbara, CA (US); George Duckett, Castaic, CA (US); Chris Zimmer, Santa Barbara, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 521 days.

(21) Appl. No.: 17/352,808

(22) Filed: Jun. 21, 2021

(65) Prior Publication Data

US 2022/0401128 A1 Dec. 22, 2022

(51) Int. Cl.
*A61B 1/06* (2006.01)
*A61B 1/00* (2006.01)
*A61B 17/34* (2006.01)

(52) U.S. Cl.
CPC ...... *A61B 17/3478* (2013.01); *A61B 1/00029* (2013.01); *A61B 1/0676* (2013.01); *A61B 1/0684* (2013.01); *A61B 2560/04* (2013.01)

(58) Field of Classification Search
CPC . A61B 1/0676; A61B 1/0684; A61B 1/00029; A61B 17/3478
USPC ........................................................ 362/574
See application file for complete search history.

(56) References Cited

U.S. PATENT DOCUMENTS

| 11,064,867 | B2 | 7/2021 | Frey et al. |
| 2014/0180001 | A1 | 6/2014 | von Grunberg et al. |
| 2015/0105618 | A1 | 4/2015 | Levy et al. |
| 2020/0100655 | A1* | 4/2020 | Morishima ........ A61B 1/00105 |
| 2022/0061645 | A1* | 3/2022 | Jochumsen .............. A61B 1/07 |
| 2023/0277049 | A1* | 9/2023 | von Wendorff ...... A61B 1/0676 600/109 |

FOREIGN PATENT DOCUMENTS

| CA | 2 798 716 A1 | 6/2013 |
| DE | 10 2016 216 160 A1 | 3/2017 |
| DE | 10 2015 220 496 A1 | 4/2017 |
| JP | 5570328 B2 | 8/2014 |

* cited by examiner

*Primary Examiner* — Christopher M Raabe
(74) *Attorney, Agent, or Firm* — Muncy, Geissler, Olds & Lowe, P.C.

(57) ABSTRACT

A trocar is provided that is adapted to insert a lighting attachment into a body cavity. The trocar connects at its distal end to the lighting attachment such that it can be pushed into the body cavity. An endoscope may then be inserted through the trocar into the body cavity. The lighting attachment is configured to detach from the trocar and attach to the endoscope head to provide additional lighting to the endoscope. The lighting attachment includes foldable lighting panels that expand when in use in order to light a wider field of view. The lighting attachment may be powered by induction coil from the endoscope.

17 Claims, 5 Drawing Sheets

TROCAR WITH DETACHABLE LIGHTING SYSTEM

BACKGROUND OF THE INVENTION

Field of the Invention

The invention relates to a trocar for assisting insertion of an endoscope into a body cavity, the trocar having a detachable, foldable lighting unit.

Description of the Background Art

The field of endoscopy has advanced quickly in recent years with the increased demand for quicker, easier, and minimally invasive techniques for abdominal surgery, biopsy, and observation. Since speed and efficiency translate into quicker recover times and overall better patient experiences, saving time and avoiding mistakes greatly improves operating success. Accordingly ergonomics and visibility play an important role in enabling a physician to quickly evaluate a patient via endoscope.

A trocar is typically used to create the initial incision into the patient and to hold open an access point to the body cavity for further instruments. In conventional trocars, no electronics are provided in the trocar. That is, it is a purely mechanical instrument formed as a hollow tube with a sharp, bladed or open tip at the distal end and a handle or thick support section at the proximal end of the hollow tube. For example, U.S. Patent Publication 2010/0318033 to Albert Lam, which discloses a simple cutting trocar, the entire disclosure of US 2010/0318033 being hereby incorporated by reference.

Endoscopes need adequate light to be supplied over a wide field of view in order for internal body tissue to be visible after the endoscope is inserted through the trocar into the body cavity. Due to the small size of the endoscope distal end, prior art endoscopes failed to provide adequate light and only had forward facing light with a narrow beam. These lighting limitations lead to limitations in the effectiveness of three-dimensional (3D) video feeds or views from the endoscope as the wider field of view is not adequately lit.

Furthermore, because endoscopes often use a trocar to avoid abrasions and tearing of tissue around the entry site, the endoscope head size is limited by the trocar inner diameter. The trocar size limitation reduces the available surface area on the head of an endoscope for added lighting. That is, after accounting for the area taken up by a pair of stereoscopic camera lenses, preferably wide angle, and perhaps an additional guiding camera, precious little space remains for artificial light which may be delivered by LED or fiber optic.

The German patent application DE 102015220496 to Frey et al., discloses one method of expanding the field of view or head size of the endoscope after insertion through a trocar, the entire disclosure of DE 102015220496 being hereby incorporated by reference. In that application, the device of Frey provides pivoting sections at the end of the endoscope head that pivot outward and expand the separation between the cameras. This specialized endoscope head, however, does not address the need for more lighting for the expanded field of view.

The US patent publication 2015/0105618 to Levy et al., discloses a ring disposed around the endoscope head to provide additional lighting and an additional camera, the entire disclosure of US 2015/0105618 being hereby incorporated by reference. The specialized ring may be added to an endoscope and the power line fed through the flushing line running through the endoscope (the flushing tube taking up even more space in the endoscope head). This specialized ring cannot be used with a trocar and is instead limited to colonoscopy since the ring changes the head of the endoscope in a way that would not fit through a trocar.

The US patent publication 2014/0180001 to von Grünberg et al., discloses a pivotable lighting system mounted on a trocar, the entire disclosure of US 2014/0180001 being hereby incorporated by reference. The trocar and an additional support structure provides two lighting systems and two cameras. The cameras pivot off the additional support on a distal end of the support and within the body cavity. For illumination a single light source is provided down the center of the trocar. While this arrangement also increases the field of view, the cameras are expanded far from the light source and will not have their field of view fully illuminated. Furthermore, the cameras in this arrangement are fixed to the rigid support passing through the trocar and, thus, the expandable cameras are not a part of a flexible endoscope head as in Levy or Frey.

Thus, the prior art devices remain difficult for surgeons to use both visually and ergonomically. The invention described below offers several features to increase usability and efficiency as well as improve the basic functions of endoscopes. The benefits of these improvements include faster and cleaner surgeries as well as better diagnostics and less visual distortions for the surgeon.

SUMMARY OF INVENTION

According to an exemplary embodiment, a lighting attachment is provided for insertion into a body cavity, the lighting attachment including a main cylindrical body having a center opening, the center opening adapted to receive an endoscope head, at least two expandable light panels connected to the main cylindrical body, and an induction coil disposed in the main cylindrical body and wrapped around the center opening. Each of the at least two expandable light panels may have at least one light emitting diode (LED) light source and the induction coil may provide current to the at least two expandable light panels. The lighting attachment may be configured to engage with a distal end of a trocar body, and the lighting attachment may disengage from the trocar body upon engagement of the lighting attachment with the endoscope head.

According to an exemplary embodiment, the endoscope head may include another inductive coil which is powered to induce the current in the induction coil of the lighting attachment.

An exemplary embodiment of the lighting attachment may include a first light panel of the at least two expandable light panels has a first spectrum with a first peak wavelength and a second light panel of the at least two expandable light panels has a second spectrum with a second peak wavelength, such that the first peak wavelength and the second peak wavelength are different. For instance, a subset of the expandable light panels may emit white light and another subset of the expandable light panels may emit blue light for photodynamic diagnosis (PDD) applications. For instance, a subset of the expandable light panels may emit white light and another subset of the expandable light panels may emit infrared (IR) light for indocyanine green (ICG) enhanced fluorescence applications. For instance, subsets of the expandable light panels may respectively emit red, green, blue, and IR wavelengths for more complex spectral selection.

The capability to select wavelengths provides the advantage of avoiding autofluorescence which can be an issue with other lighting systems in fluorescence imaging applications. The expandable light panels may toggle or strobe between various wavelengths on a frame-by-frame basis for time-sequential imaging or may synchronize with a camera shutter to capture separate frames or images with white light and with fluorescence.

An exemplary embodiment of the lighting attachment may include that the at least two expandable light panels are disposed in a folded configuration when the lighting attachment is engaging with the trocar body. Further the endoscope head may control the at least two expandable light panels to expand from the folded configuration after disengagement from the trocar body.

An exemplary embodiment may provide that when the lighting attachment is engaged with the trocar body, a circumferential surface of the lighting attachment and the at least two expandable light panels are enclosed in the trocar body. The lighting attachment may mechanically engage with the trocar body or trocar. The lighting attachment may magnetically engage with the endoscope head and/or the trocar body.

An exemplary embodiment may include a lighting attachment with a connection engaging the endoscope head with the lighting attachment that allows the lighting attachment to follow the endoscope head during movement within the body cavity. The at least two expandable light panels of the lighting attachment may have a pivot angle that is controlled by the endoscope head to light a field of view of at least two cameras in the endoscope head. The at least two expandable light panels may be connected to the main cylindrical body via hinges and a movement of the hinges may be powered by the induction coil.

A trocar with the trocar body may be configured to engage the lighting attachment and further configured to allow the endoscope head to pass through a central through hole of the trocar. A proximal surface of the main cylindrical body of the lighting attachment may abut the distal end of the trocar body. A diameter of the lighting attachment may be configured to be greater than a diameter of the trocar body. The endoscope head may be configured to pass through the center opening of the main cylindrical body of the lighting attachment. The trocar body may be adapted to be inserted into the body cavity.

Further scope of the applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION

Figure 1:
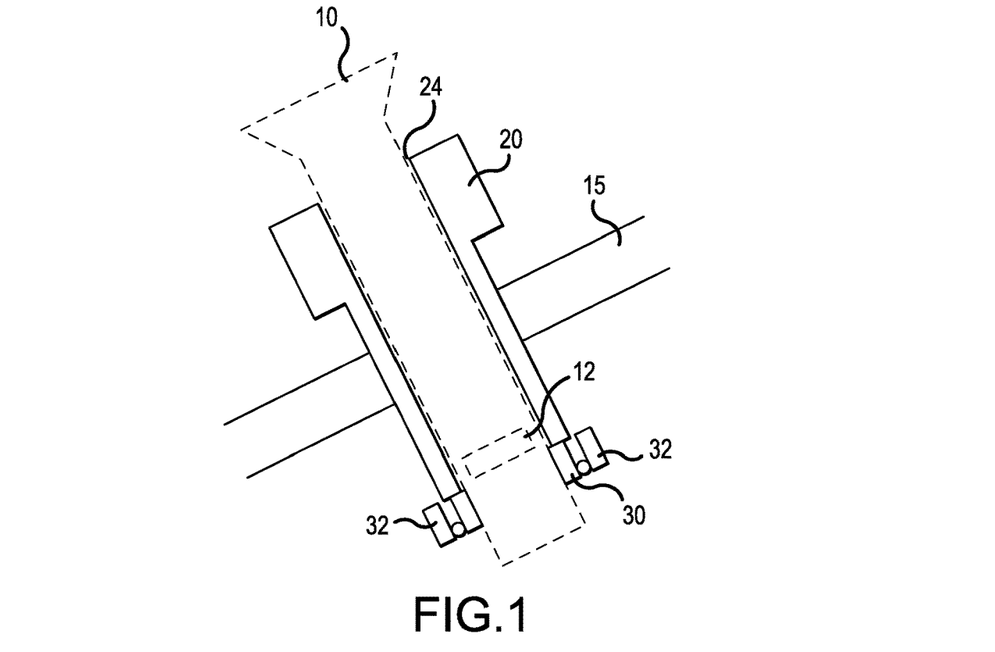
FIG. 1 shows a cross section of a trocar according to an implementation.

In the exemplary design shown in FIG. 1 illustrates a trocar 20 inserted through a body cavity lining 15 (e.g., peritoneal lining, muscles, skin). The trocar 20 may include cutting attachments, suction tubes, flushing tubes, and other features to perform surgical preparation tasks. After the trocar 20 and lighting attachment 30 have been inserted and the body cavity prepped, then an endoscope 10 may be inserted through the central opening or through hole 24 of the trocar 20. The endoscope 10 may be sized to fit exactly or substantially form fittingly with the diameter of the central opening 24 of the trocar 20.

In medicine, endoscopes may provide two-dimensional (2D) views, three-dimensional views (3D), or stereoscopic views of the inside of a body cavity, intestine, throat, etc. and may include some biopsy functionality. The endoscope 10 may be formed as a flexible cylindrical pipe including a lighting element (e.g. fiber optic or powered light emitting diode), two or more cameras or optical channels, and one or more biopsy tools. The endoscope 10 may include a magnet 12 in the distal portion of the neck and a view port at the proximal end (in the case of optical channels). The endoscope may simply transmit the digital feeds from the cameras via one or more wires to displays.

A lighting attachment 30 is illustrated at the distal end of the trocar 20. The lighting attachment 30 may be engaged or detachably connected to the trocar 20 via a clasp, a snap fitting, or the like. The lighting attachment 30 may be cylindrical and have a through hole or central opening matching the diameter of the central opening 24 of the trocar 20. Accordingly, the endoscope 10 may also fit form fittingly, correspondingly, and/or snugly into the central opening of the lighting attachment 30. The lighting attachment 30 has foldable planes or wings 32 on two, three, four, or more points on the circumference of its cylindrical body.

The endoscope 10 is inserted towards the distal end of the trocar 20 and into the body cavity. The endoscope 10 may include a head or a portion of its head with a smaller diameter than the long neck portion of the endoscope 10. In this configuration, the central opening of the lighting attachment 30 may be sized, as shown in FIG. 1, only allow the smaller head through and will then catch on the lip or gradient on the outer surface of the endoscope at the transition from head to the larger neck. Thus, when the endoscope 10 is pushed through the central opening of the lighting attachment 30, the transition to the larger neck engages the lighting attachment 30 and pushes it away from the trocar 20 into the body cavity.

Figure 2:
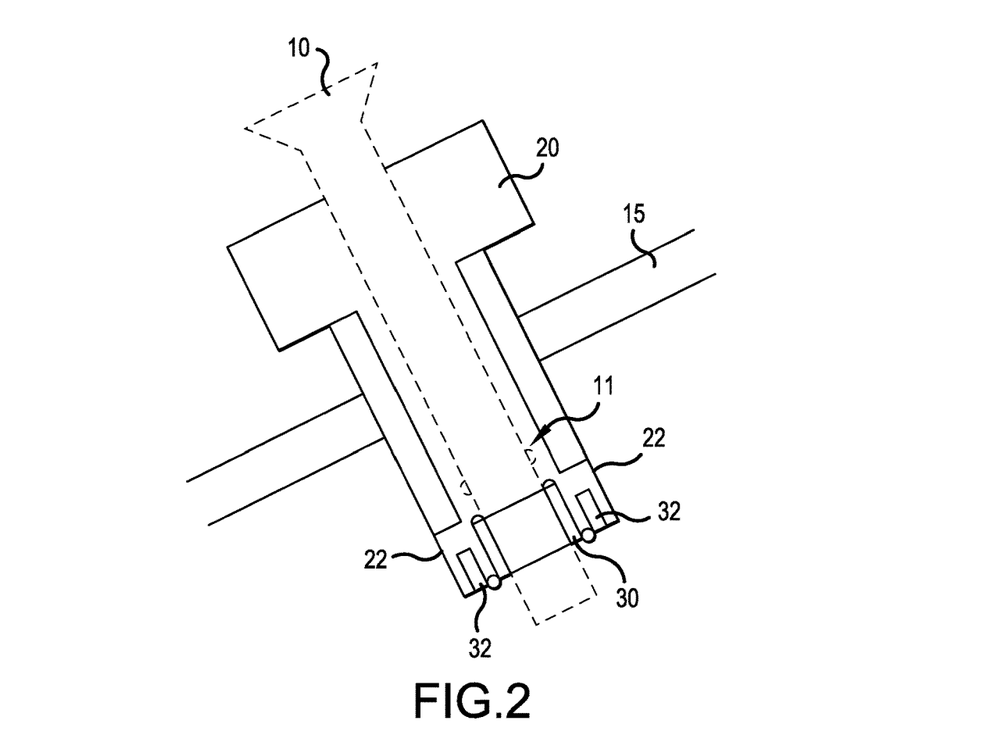
FIG. 2 shows a cross section of a trocar according to an implementation.

In addition, the magnet 12 in the endoscope head may secure the lighting attachment 30 so that reverse movement out of the body cavity does not leave the lighting attachment 30 behind, the magnet 12 may be an electromagnet. The electromagnet 12 may also be adapted to charge the lighting attachment 30 via the induction coil 38 in the lighting attachment. Alternatively, the endoscope head may mechanically engage (e.g. by detent 11 as shown in FIG. 2) the lighting attachment 30 in a secure manner (e.g. snap fit) that may only be disengaged by a mechanical engagement or detent release mechanism on the trocar 20 upon retraction of the head back into the trocar 20. This mechanical engagement is illustrated in FIG. 2 as detent 11 which engages with the inner surface of the central opening in the lighting attachment 30.

FIG. 2 illustrates a trocar body different from that of the trocar 20 of FIG. 1, where the outer cylindrical wall 22 of the trocar 20 of FIG. 2 encloses the circumferential sides of the lighting attachment 30 including the lighting panels 32. This enclosing wall 22 provides protection for the lighting attachment 30 upon insertion of the trocar 20 so that it does not catch on body tissue. The trocar body of FIG. 2 may be longer and/or wider than that of FIG. 1. While the main cylindrical body of the lighting attachment 30 of FIG. 1 is shown as offset from the inner through hole of the trocar 20, that need not be the case. For example, the inner/central opening of the lighting attachment 30 may have a same diameter or size as the trocar 20 so as to accommodate a larger endoscope 10. Similarly, the endoscope neck may be larger above the engagement point with the lighting attachment 30. The size and shape of the trocar 20 especially the expanded, proximal head portion of the trocar 20 may be shaped differently (e.g. rounded corners, raised center, integral grips or handles, etc.) without deviating from the features at the distal end disclosed herein.

Figure 3:
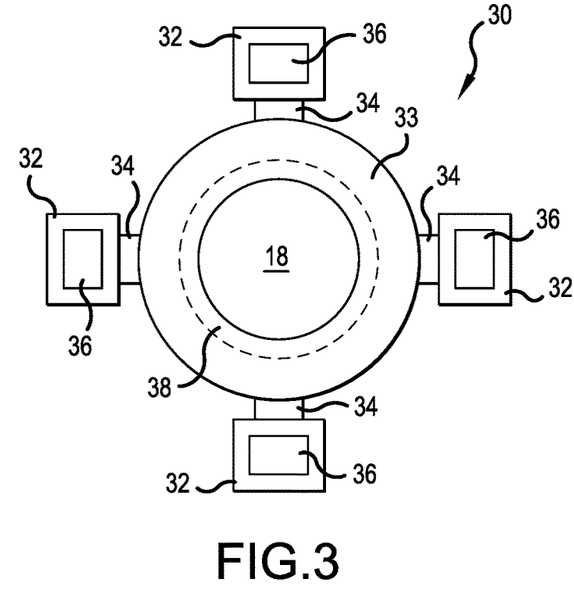
FIG. 3 shows a lighting attachment for a trocar and/or an endoscope according to an implementation.

The view of the lighting attachment 30 provided in FIG. 3 shows the main cylindrical body 33 with central opening 18 and four light panels 32 in an expanded position. The light panels 32 are joined to the main cylindrical body 33 by hinges 34 which may be rotated to move the light panels 32 from a folded position to an expanded position. Each light panel may include one or more light emitting diodes (LED) or blocks of LEDs 36 disposed in a plane of the light panel 32 on an outer/lower surface. The LEDs may be powered via wires and current passing through the hinges 34. Other connections for passing current from the main cylindrical body 33 through the hinges 34 may be used. The light panels 32 may be illuminated when not fully expanded so as to expand the field of view being illuminated around the head of the endoscope 10.

The main cylindrical body 33 of the lighting attachment 30 includes an induction coil 38 wrapped around or surrounding the central opening 18 and configured to generate current by induction of an alternating current (AC) in the induction coil 38. The induction coil 38 may also engage with magnet 12 of the endoscope 10. The induction coil 38 may power the hinges 34, the LEDs 36 and a control unit for the LEDs. The LEDs 36 may be of different wavelengths such that, for example, two are of a first wavelength (i.e. visible light) and two are of a different second wavelength (e.g. near infrared), where the first and second wavelengths have different spectra or different peak wavelengths. The hinges 34 may be rotated via threaded screws powered by a motor or by muscle wire (e.g. Nitinol) or an electroactive polymer that expands/contracts and unfolds (e.g. straightens) the lighting panels 32 upon electrification or the application of current to the wire. Additional lighting panels may also be connected to the main body 33 between the four shown. Likewise, fewer lighting panels 32, such as two panels, may be provided.

Figure 4:
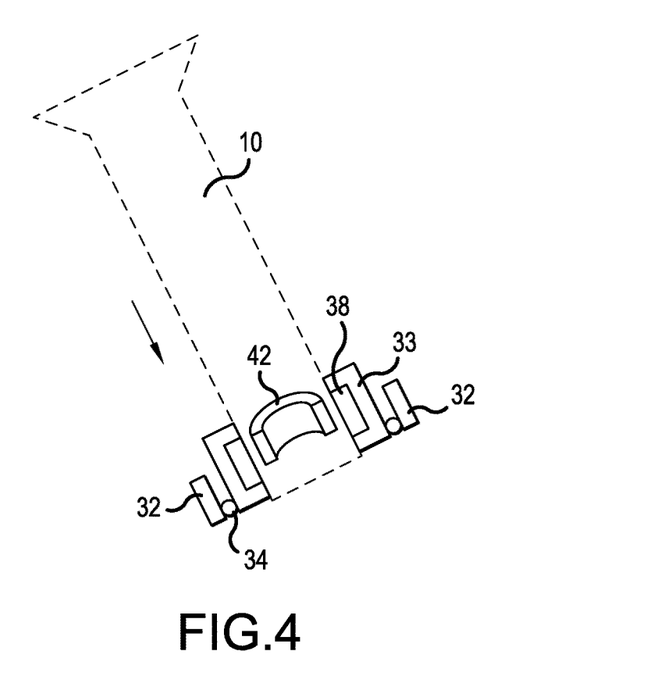
FIG. 4 shows a cross section of an endoscope and a corresponding cross section of a lighting attachment connected to the endoscope according to an implementation.

In FIG. 4, the lighting attachment 30 is depicted connecting with the distal head of the endoscope 10 with the insertion direction shown. In addition, in this cross sectional view, the induction coil 38 is shown together with a corresponding induction coil 42 in the endoscope 10. The induction coil 42 induces AC current in the induction coil 38 of the lighting attachment 30. This induced current may be rectified or may be used to directly power a light source in the lighting panels 32. The endoscope 10 may be powered by a wired AC or DC power source connected to a proximal end of the endoscope 10, the power source providing current to the inductor 42.

Figure 5A:
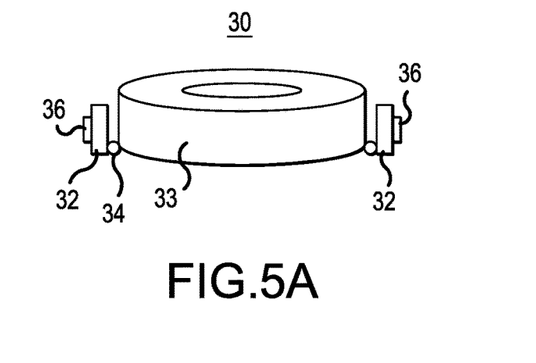
FIG. 5A shows a lighting attachment in a folded configuration according to an implementation.

In FIG. 5A, the lighting attachment 30 is shown with the main cylindrical body 33, the hinges 34, and the LEDs 36 on the light panels 32 in a perspective view. The perspective view illustrates the hollow, cylindrical shape of the main body 33. The main body 33 may also be a toroid or similar shape. The configuration of the lighting attachment 30 in FIG. 5A is a folded configuration with the sides of the light panels 32 opposite the LEDs 36 being flush or abutting the circumferential surface of the main body 33. Even in this configuration, the LEDs may be controlled to turn on or may be energized by the induced energy of the inductor coil 38.

Figure 5B:
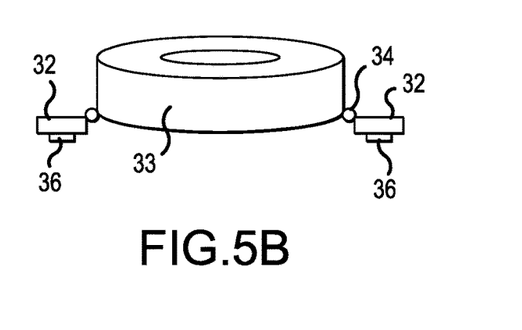
FIG. 5B shows a lighting attachment in an expanded configuration according to an implementation.

In FIG. 5B, the lighting attachment 30 is shown in perspective view in an expanded configuration. The light panels 32 may be rotated even further (angularly) from the outer circumferential surface of the main body 33 in order to focus or direct more light towards a central (axial) point in front of the endoscope 10. The two LEDs 36 on either side may be of different wavelengths. Indeed, one may be configured to emit ultraviolet or infrared wavelengths to illuminate a dye or other artificial marker in the body cavity. The rotation angle or fold angle of each light panel 32 may be separately controlled and may be controlled to correspond to a viewing angle or position of a corresponding camera in the endoscope. The rotation angle or fold angle of each light panel 32 may be controlled, manually or automatically, to follow a swivel direction or viewing zone of the endoscope 10 or the operation location of a biopsy tool. The number of light panels 32 illustrated in FIGS. 5A and 5B are exemplary and may be any number or may be combined with the lighting attachment 30 of FIG. 3.

For instance, a subset of the expandable light panels may emit white light and another subset of the expandable light panels may emit blue light for photodynamic diagnosis (PDD) applications. For instance, a subset of the expandable light panels may emit white light and another subset of the expandable light panels may emit infrared (IR) light for indocyanine green (ICG) enhanced fluorescence applications. For instance, subsets of the expandable light panels may respectively emit red, green, blue, and IR wavelengths for more complex spectral selection. The expandable light panels may toggle, alternate, or strobe between various wavelengths on a frame-by-frame basis for time-sequential imaging by a camera of the endoscope 10. One or more of the expandable light panels may synchronize illumination in one or more wavelengths with a camera shutter or capture sequence so as to capture separate frames or images with different wavelengths (e.g. white light and with fluorescence).

Figure 6A:
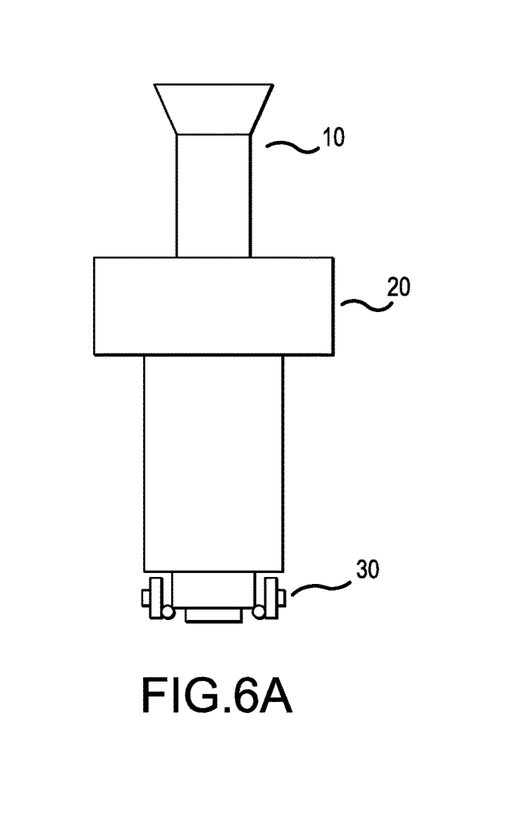
FIG. 6A shows a trocar and lighting attachment with an endoscope inserted to one position according to an implementation.
Figure 6B:
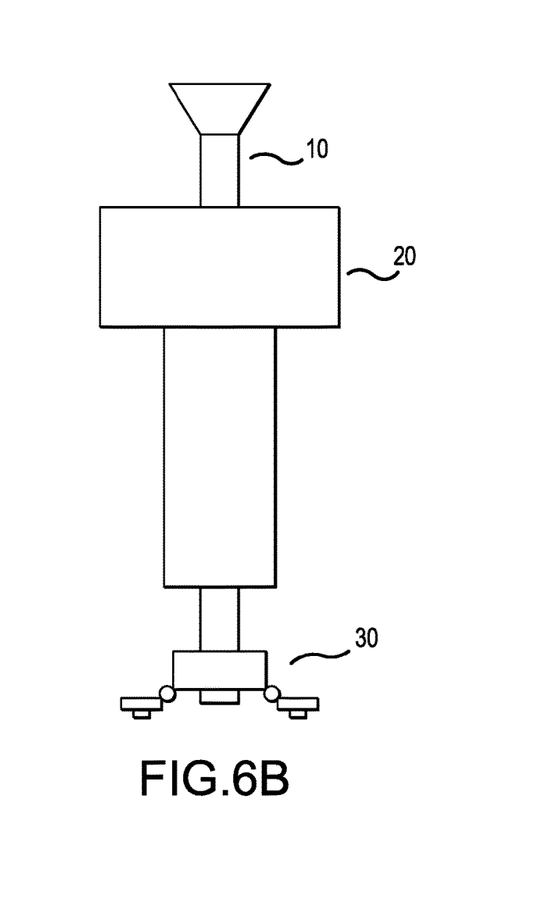
FIG. 6B shows a trocar and a lighting attachment with an endoscope inserted to another position according to an implementation.

In FIG. 6A, the endoscope 10, the trocar 20, and lighting attachment 30 are depicted in a side view of the assembly where the endoscope 10 has been partially inserted into the trocar 20 so as to engage the lighting attachment 30 without separating the lighting attachment 30 from the trocar 20. In this position, the lighting attachment 30 is in a folded configuration. The length of the endoscope 10 in FIGS. 6A and 6B is purely for illustration and may be much longer and flexible or not rigid as shown. In FIG. 6B, the endoscope 10 is inserted further through the trocar 20 pushing the lighting attachment 30 to disengage or disconnect from the trocar 20. The trocar 20 may power an electromagnet in the trocar that provides the engaging or connective force attaching the lighting attachment 30 to the trocar 20.

In FIG. 6B the lighting attachment 30 is securely connected to the endoscope head via mechanical or electromagnetic mechanisms. In addition, the light panels of the lighting attachment 30 have been controlled by the endoscope 10 or the light attachment 30 to unfold or expand into a horizontal position. Upon retraction of the endoscope 10 back through the trocar 20, the lighting attachment 30 may return to the position shown in FIG. 6A and may be controlled by internal controls, the endoscope 10, or the trocar 20 to return to a folded position. The lighting attachment 30 may need to be in a folded configuration for removal back out of the surgical incision.

Figure 7:
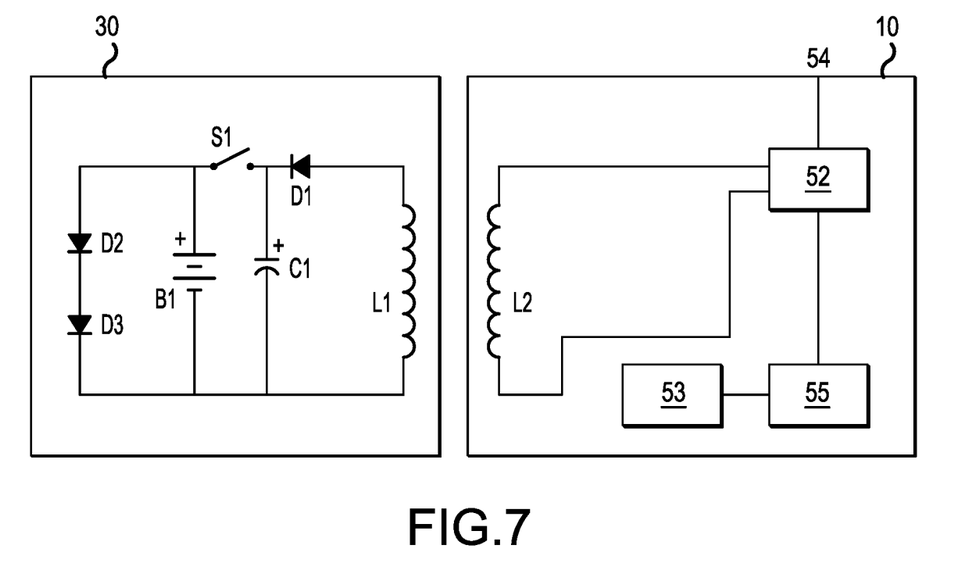
FIG. 7 shows an electrical schematic for power transmission between the endoscope and the lighting attachment according to an implementation.

In FIG. 7 the physical and electrical interfaces between the endoscope 10 and the lighting attachment 30 are depicted in schematic form. The inner cylindrical wall of the central opening 18 may be in aligned and in close proximity to the outer cylindrical wall of the endoscope 10. The two walls may abut or may be flush. The circuit depicted in the lighting attachment 30 is an exemplary simplified design. The endoscope 10 receives power and control signals via connector 54 and may transmit video signals via the connector 54 as well, connector 54 may have multiple ports.

In the head of the endoscope 10, the connector 54 is electrically connected to a control unit 52 which is connected to one or more cameras 55 and one or more lighting devices 53. Two of the cameras 55 may form a stereoscopic or 3D view while another of the cameras 55 may provide a 2D view for navigation. The one or more lighting devices 53 are separate from the light panels 32 and, preferably are not needed. Nevertheless, the lighting attachment 30 may be configured to operate with and enhance endoscopes that already have some lighting. The cameras 55 and the lighting devices 53 may include optical lenses on an exterior of the endoscope head. The control unit 52 also may provide AC power to the inductor coil L2/42 of the endoscope 10 which creates electromagnetic waves to induce current in the corresponding inductor coil L1/38 of the lighting attachment 30.

The induced AC current in the inductor coil 38/L1 of the lighting attachment 30 is rectified by a rectifying diode D1 and may power a capacitor C1 to stabilize the power in the circuit. A switch S1 may control the power supply to the battery B1 and to LEDs or diodes D2 and D3. The diodes D2 and D3 may be in separate light panels 32, for example. Diodes D2 and D3 may alternatively be arranged in parallel. This circuit does not include actuators for rotating the hinges 34 which may be powered by the induced current. In this circuit, the induced current may charge the battery B1 when the switch S1 is closed, and the battery B1 may power the LEDs D2 and D3 even when the switch S1 is open. It should be noted that after passing through the rectifying diode D1, the current is a DC current which is compatible with the diodes D2 and D3 and the battery B1.

Figure 8:
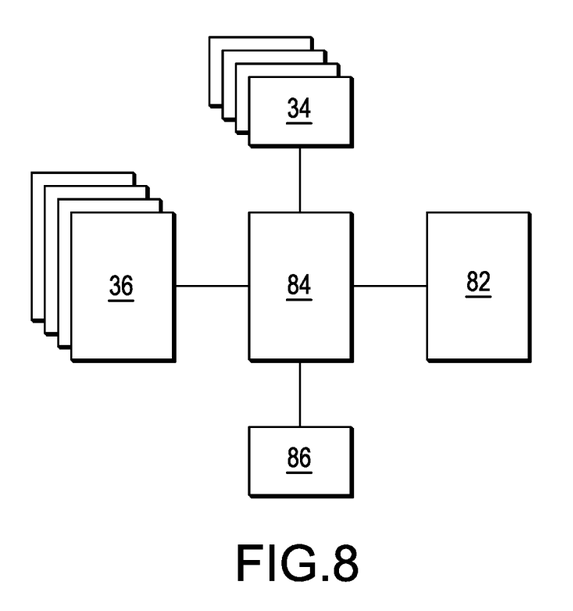
FIG. 8 shows a system for powering and controlling the lighting attachment according to an implementation.

A more involved and versatile system of the lighting attachment 30 is shown in FIG. 8 where an inductor coil 82 provides power to a control unit 84 and a battery 86. The control unit 84 controls and/or supplies power to the LEDs 36 and the rotating or flexible hinges 34 to pivot the light panels 32. The control unit 84 may also provide charging control and discharge control of the battery 86. The control unit 84 may decode or detect signals to open or expand the light panels 32. These signals may be received over the inductor coil 82/38 or via wireless signals to a receiver on the lighting attachment 30. This control system of FIG. 8 may be controlled by the endoscope 10 so as to direct lighting according to the needs of the surgeon or according to the field of view of the endoscope 10.

Figure 9:
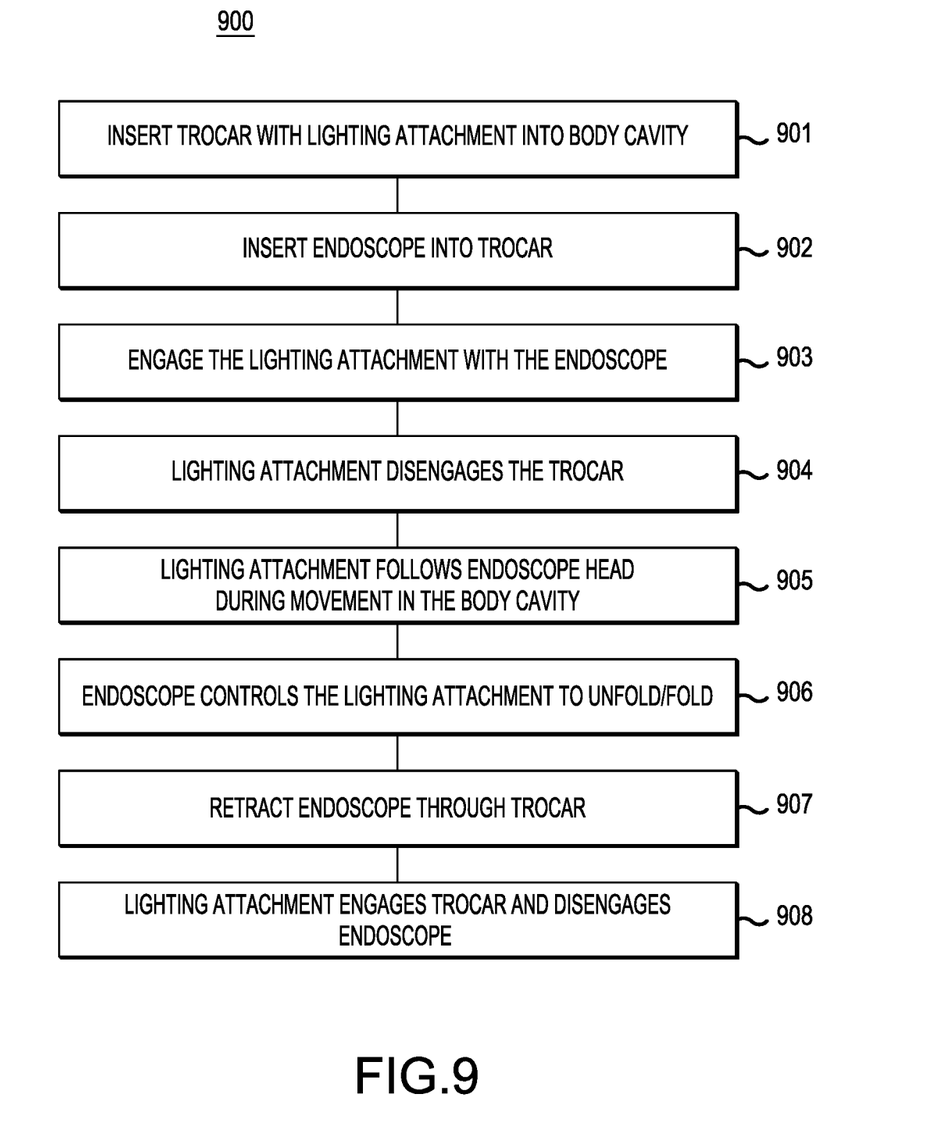
FIG. 9 shows a process by which the lighting attachment operates with an endoscope and a trocar according to an implementation.

A process 900 as illustrated in FIG. 9 may begin with the insertion of a trocar 20 with the lighting attachment into a body cavity, at 901. After the trocar has been inserted and the body cavity prepped, the endoscope 10 may be inserted into the trocar 20 at 902. At 903, the endoscope 10 may be inserted sufficiently so as to engage the lighting attachment 30 at the distal end of the trocar 20. As a result of the engagement or connection between the endoscope 10 and the lighting attachment 30, the lighting attachment 30 disengages the trocar 20 (or the trocar 20 disengages) leaving the lighting attachment 30 connected to the endoscope at its head at 904.

Once the lighting attachment 30 is connected to the head of the endoscope 10, the lighting attachment 30 may follow the endoscope 10 as it traverses or is extended into the body cavity at 905. The endoscope 10 may control the lighting attachment 30 to unfold the light panels 32 when additional light is needed or a larger field of view is being observed at 906. The angled lighting panels 32 provide illumination to a much wider field of view than built-in lighting available for endoscopes. The improved, brighter lighting to the wider field of view (e.g. greater than 180 degrees) about the endoscope head may be advantageous in single-site laparoscopic appendectomies (SSLA) or natural orifice transluminal endoscopic surgery (NOTES).

The endoscope 10 may control the LEDs 36 to be switched ON or OFF. After the surgeon has completed the operation or the observation, the surgeon may operate the endoscope 10 to fold the light panels 32 into a folded configuration for retraction at 906. At 907, the endoscope 10 may be retracted through the trocar 20. When the lighting attachment 30 and endoscope head have retracted to the distal end of the trocar 20, the lighting attachment 30 engages the trocar 20 and the endoscope continues to slide out of the body cavity through the trocar at 908. Likewise and substantially simultaneously, the lighting attachment disengages or disconnects from the endoscope. The connection with the trocar 20 may be a mechanical or electromagnetic connection (e.g. a detent or snap fit). Once the lighting attachment 30 is secured to the trocar and the endoscope 10 is removed, the process 900 may be repeated starting with 902. The steps or parts of process 900 need not be only linear as many of the processes or progressions from one part to another are reversible. Indeed, the engagement and disengagement of the endoscope/trocar with the lighting attachment 30 is advantageously reversible so that the trocar and lighting attachment arrangement is re-usable.

The mating of the trocar and the ring body may be performed in situ, that is within the body cavity. Specifically, the lighting attachment 30 may be introduced into the patient's body through a second access point into the body cavity via a second trocar. The lighting attachment 30 may then be slid in situ onto the distal end of the trocar 20 to be used for the endoscope 10. The lighting attachment 30 may attach to the second trocar and the trocar 20 via magnetic force from electromagnets in the distal end of each trocar.

The physical features of the trocars, endoscopes, and external devices (e.g. displays) are non-limiting examples. The lighting attachment 30 may be used with trocars and endoscopes of other configurations so long as they are adapted to attach to the lighting attachment 30 in one of the many ways described herein for attachment. In particular, the outside diameter of the lighting attachment 30 in the folded configuration may be sized to match the outside diameter of the trocar 20, or the central opening 18 of the lighting attachment 30 may be sized to match the through hole 24 of the trocar 20, or both. Likewise, one or more of the connection mechanisms disclosed herein for the lighting attachment may be provided on a single lighting attachment.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A lighting attachment for insertion into a body cavity, the lighting attachment comprising:
   a main cylindrical body having a center opening, the center opening adapted to receive an endoscope head;
   at least two expandable light panels connected to the main cylindrical body, each of the at least two expandable light panels having at least one light source; and
   an induction coil disposed in the main cylindrical body and wrapped around the center opening, the induction coil providing current to the at least two expandable light panels,
   wherein the lighting attachment is configured to engage with a distal end of a trocar body, and
   wherein, the lighting attachment disengages from the trocar body upon engagement of the lighting attachment with the endoscope head.

2. The lighting attachment according to claim 1, wherein the endoscope head includes another inductive coil which is powered to induce the current in the induction coil of the lighting attachment.

3. The lighting attachment according to claim 1, wherein a first light panel of the at least two expandable light panels has a first spectrum with a first peak wavelength and a second light panel of the at least two expandable light panels has a second spectrum with a second peak wavelength, and wherein the first peak wavelength and the second peak wavelength are different.

4. The lighting attachment according to claim 1, wherein the at least two expandable light panels are disposed in a folded configuration when the lighting attachment is engaging with the trocar body.

5. The lighting attachment according to claim 4, wherein the endoscope head controls the at least two expandable light panels to expand from the folded configuration after disengagement from the trocar body.

6. The lighting attachment according to claim 1, wherein, when the lighting attachment is engaged with the trocar body, a circumferential surface of the lighting attachment and the at least two expandable light panels are enclosed in the trocar body.

7. The lighting attachment according to claim 1, wherein the lighting attachment mechanically engages with the trocar body.

8. The lighting attachment according to claim 1, wherein the lighting attachment magnetically engages with the endoscope head.

9. The lighting attachment according to claim 1, wherein a connection engaging the endoscope head with the lighting attachment allows the lighting attachment to follow the endoscope head during movement within the body cavity.

10. The lighting attachment according to claim 1, wherein a pivot angle of each of the at least two expandable light panels is controlled by the endoscope head to light a field of view of at least two cameras in the endoscope head.

11. A trocar with the trocar body configured to engage the lighting attachment according to claim 1, the endoscope head passing through a central through hole of the trocar.

12. The lighting attachment according to claim 1, wherein a proximal surface of the main cylindrical body abuts the distal end of the trocar body.

13. The lighting attachment according to claim 1, wherein a diameter of the lighting attachment is greater than a diameter of the trocar body.

14. The lighting attachment according to claim 1, wherein the endoscope head passes through the center opening of the main cylindrical body.

15. The lighting attachment according to claim 1, wherein the trocar body is adapted to be inserted into the body cavity.

16. The lighting attachment according to claim 1, wherein the at least two expandable light panels are connected to the main cylindrical body via hinges, a movement of the hinges being powered by the induction coil.

17. The lighting attachment according to claim 1, wherein the at least one light source is a light emitting diode (LED).

\* \* \* \* \*